(12) United States Patent
Pancheri

(10) Patent No.: US 11,425,911 B2
(45) Date of Patent: *Aug. 30, 2022

(54) METHOD FOR DISINFECTION OF ITEMS AND SPACES

(71) Applicant: Markesbery Blue Pearl LLC, Hebron, KY (US)

(72) Inventor: Eugene Joseph Pancheri, Cincinnati, OH (US)

(73) Assignee: MARKESBERY BLUE PEARL LLC, Hebron, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/912,734

(22) Filed: Jun. 26, 2020

(65) Prior Publication Data

US 2020/0390103 A1 Dec. 17, 2020

Related U.S. Application Data

(63) Continuation of application No. 16/202,269, filed on Nov. 28, 2018, now abandoned, and a continuation-in-part of application No. 16/755,361, filed as application No. PCT/US2018/055367 on Oct. 11, 2018, application No. 16/912,734, filed on Jun. 26, 2020, which is a continuation-in-part of application No. 16/747,621, filed on Jan. 21, 2020, which is a continuation of application No. 16/198,570, filed on Nov. 21, 2018, now Pat. No. 10,603,396, which is a continuation-in-part of application No. PCT/US2017/034519, filed on May 25, 2017.

(60) Provisional application No. 62/591,812, filed on Nov. 29, 2017, provisional application No. 62/570,808, filed on Oct. 11, 2017, provisional application No. 62/591,588, filed on Nov. 28, 2017, provisional application No. 62/591,591, filed on Nov. 28, 2017.

(51) Int. Cl.

| A01N 59/00 | (2006.01) |
| A01N 25/02 | (2006.01) |
| A01N 59/12 | (2006.01) |
| A01N 65/24 | (2009.01) |
| A61L 2/22 | (2006.01) |
| A61L 2/18 | (2006.01) |

(52) U.S. Cl.
CPC ............ *A01N 59/00* (2013.01); *A01N 25/02* (2013.01); *A01N 59/12* (2013.01); *A01N 65/24* (2013.01); *A61L 2/186* (2013.01); *A61L 2/22* (2013.01); *A61L 2202/15* (2013.01); *A61L 2202/24* (2013.01); *A61L 2202/25* (2013.01)

(58) Field of Classification Search
CPC .................................................. A01N 59/00
See application file for complete search history.

(56) References Cited

U.S. PATENT DOCUMENTS

| 3,485,588 | A | 12/1969 | Fouts |
| 5,743,251 | A | 4/1998 | Howell et al. |
| 5,772,971 | A | 6/1998 | Murphy et al. |
| 6,234,167 | B1 | 5/2001 | Cox et al. |
| 6,491,233 | B2 | 12/2002 | Nichols |
| 6,501,052 | B2 | 12/2002 | Cox et al. |
| 6,516,796 | B1 | 2/2003 | Cox et al. |
| 6,557,552 | B1 | 5/2003 | Cox et al. |
| 6,568,390 | B2 | 5/2003 | Nichols et al. |
| 6,640,050 | B2 | 10/2003 | Nichols et al. |
| 6,681,769 | B2 | 1/2004 | Sprinkel, Jr. et al. |
| 6,681,998 | B2 | 1/2004 | Sharpe et al. |
| 6,692,694 | B1 | 2/2004 | Curry et al. |
| 6,701,921 | B2 | 3/2004 | Sprinkel, Jr. et al. |
| 6,715,487 | B2 | 4/2004 | Nichols et al. |
| 6,766,220 | B2 | 7/2004 | McRae et al. |
| 6,772,757 | B2 | 8/2004 | Sprinkel, Jr. et al. |
| 6,799,572 | B2 | 10/2004 | Nichols et al. |
| 6,804,458 | B2 | 10/2004 | Sherwood et al. |

(Continued)

FOREIGN PATENT DOCUMENTS

| CN | 2357810 Y | 1/2000 |
| CN | 101801423 A | 8/2010 |

(Continued)

OTHER PUBLICATIONS

Multi-Clean (Treating Pathogens: Electrostatic Spraying of Disinfectant Solutions) May 2016.
Bell et al., "Reduction of foodborne micro-organisms on beef carcass tissue using acetic acid, sodium bicarbonate, and hydrogen peroxide spray washes", Oct. 1, 1997, Food Microbiology vol. 14, No. 5, p. 439-448 (10 pages).
Helal et al., "Antimicrobial Activity of Some Essential Oils Against Microorganisms Deteriorating Fruit Juices", Mycobiology pp. 219-229, vol. 34 No. 4, 2006 (11 pages).
Zhao, Xuebing, et al., "Preparation of Peracetic Acid from Hydrogen Peroxide Part I : Kinetics for Peracetic Acid Synthesis and Hydrolysis", Journal of Molecular Catalysis A : Chemical, vol. 271, Mar. 12, 2007 (7 pages).

(Continued)

*Primary Examiner* — Sarah Alawadi
(74) *Attorney, Agent, or Firm* — Daniel F. Nesbitt; Nesbitt IP LLC

(57) ABSTRACT

This disclosure provides a method of disinfecting a surface within an area, comprising the steps of: a) dispersing into the area a multiplicity of droplets of a first aqueous composition comprising a first iodine reactant compound that is either a peroxide compound or an iodine salt compound: b) allowing sufficient time for the first aqueous composition to distribute throughout the area, and to deposit and coalesce into a layer upon the surface: c) dispersing into the area a multiplicity of droplets of a second aqueous composition comprising a second iodine reactant compound that is the other of the first iodine reactant compound, and: d) again allowing sufficient time for the droplets of the second aqueous composition to deposit onto the coalesced layer of the first aqueous composition, thereby forming iodine and other iodine biocides in situ and disinfecting the surface.

20 Claims, No Drawings

(56) References Cited

U.S. PATENT DOCUMENTS

| | | | |
|---|---|---|---|
| 6,883,516 | B2 | 4/2005 | Hindle et al. |
| 6,916,493 | B2 | 7/2005 | Morelli et al. |
| 6,923,179 | B2 | 8/2005 | Gupta et al. |
| 7,040,314 | B2 | 5/2006 | Nguyen et al. |
| 7,077,130 | B2 | 7/2006 | Nichols et al. |
| 7,117,867 | B2 | 10/2006 | Cox et al. |
| 7,128,067 | B2 | 10/2006 | Byron et al. |
| 7,147,170 | B2 | 12/2006 | Nguyen et al. |
| 7,159,507 | B2 | 1/2007 | Grollimund et al. |
| 7,163,014 | B2 | 1/2007 | Nichols et al. |
| 7,167,776 | B2 | 1/2007 | Maharajh et al. |
| 7,173,222 | B2 | 2/2007 | Cox et al. |
| 7,351,684 | B2 | 4/2008 | Tichy et al. |
| 7,367,334 | B2 | 5/2008 | Faison, Jr. et al. |
| 7,373,938 | B2 | 5/2008 | Nichols et al. |
| 7,400,940 | B2 | 7/2008 | McRae et al. |
| 7,473,675 | B2 | 1/2009 | Tichy et al. |
| 7,500,479 | B2 | 3/2009 | Nichols et al. |
| 7,534,756 | B2 | 5/2009 | Tichy et al. |
| 7,658,953 | B2 | 6/2010 | Bobbert |
| 7,743,766 | B2 | 6/2010 | Gupta et al. |
| 8,034,759 | B2 | 10/2011 | Man et al. |
| 8,110,538 | B2 | 2/2012 | Martin et al. |
| 8,442,390 | B2 | 5/2013 | Nichols et al. |
| 8,679,527 | B2 | 3/2014 | Keiji et al. |
| 8,696,986 | B2 | 4/2014 | Rovison, Jr. et al. |
| 8,716,339 | B2 | 5/2014 | Larson et al. |
| 8,746,597 | B2 | 6/2014 | Sides |
| 8,772,218 | B2 | 7/2014 | Cunningham et al. |
| 8,789,716 | B2 | 7/2014 | Larson et al. |
| 8,883,074 | B2 | 11/2014 | Bobbert |
| 8,987,331 | B2 | 3/2015 | Larson et al. |
| 9,044,403 | B2 | 6/2015 | Shultz |
| 9,050,384 | B2 | 6/2015 | Grant et al. |
| 9,061,300 | B2 | 6/2015 | Belcastro et al. |
| 9,192,909 | B2 | 11/2015 | Kraus et al. |
| 9,241,483 | B2 | 1/2016 | Golden et al. |
| 9,447,448 | B1 | 9/2016 | Kozloski et al. |
| 9,481,460 | B1 | 11/2016 | Kozloski et al. |
| 9,540,248 | B2 | 1/2017 | Maiti et al. |
| 9,936,695 | B1 | 4/2018 | Bingham et al. |
| 2004/0120844 | A1 | 6/2004 | Tribelsky et al. |
| 2005/0238631 | A1 | 10/2005 | Burwell |
| 2006/0289354 | A1 | 12/2006 | Zhou et al. |
| 2007/0231200 | A1 | 10/2007 | Lin et al. |
| 2007/0262478 | A1 | 11/2007 | Price et al. |
| 2008/0000931 | A1 | 1/2008 | Tichy et al. |
| 2008/0241269 | A1* | 10/2008 | Velasquez ............ A23L 3/3463 424/520 |
| 2009/0246336 | A1 | 10/2009 | Burnett et al. |
| 2010/0316530 | A1 | 12/2010 | Morgantini et al. |
| 2013/0199539 | A1 | 8/2013 | Webster |
| 2013/0316055 | A1 | 11/2013 | Holt |
| 2014/0178249 | A1 | 6/2014 | Tichy et al. |
| 2014/0238445 | A1 | 8/2014 | Stokes et al. |
| 2014/0275267 | A1 | 9/2014 | Beug-Deeb et al. |
| 2014/0328949 | A1 | 11/2014 | Adams et al. |
| 2014/0378544 | A1 | 12/2014 | Kraus et al. |
| 2015/0102061 | A1 | 4/2015 | Larson et al. |
| 2015/0297770 | A1 | 10/2015 | Larson et al. |
| 2016/0022850 | A1 | 1/2016 | Tsai et al. |

FOREIGN PATENT DOCUMENTS

| | | |
|---|---|---|
| CN | 103635207 A | 3/2014 |
| CN | 104434669 A | 3/2015 |
| CN | 105147540 A | 12/2015 |
| CN | 106509445 A | 3/2017 |
| EP | 0411970 A1 | 2/1991 |
| EP | 2724614 A1 * | 10/2012 |
| GB | 2257630 A | 1/1993 |
| GB | 2469018 A | 10/2010 |
| JP | 2000-60418 A | 2/2000 |
| JP | 2002-505658 A | 2/2002 |
| JP | 2009-505655 A | 2/2009 |
| JP | 2013-515072 A | 5/2013 |
| WO | 9746626 A1 | 12/1997 |
| WO | 0128511 A2 | 4/2001 |
| WO | 0134211 A2 | 5/2001 |
| WO | 2008021441 | 2/2008 |
| WO | 2010056871 A2 | 5/2010 |
| WO | 2011044916 A1 | 4/2011 |
| WO | 2011139300 A2 | 11/2011 |
| WO | 2015074144 A1 | 5/2015 |
| WO | 2016165793 A1 | 10/2016 |
| WO | 2017205649 A1 | 11/2017 |
| WO | 2018223080 A1 | 12/2018 |
| WO | 2019075176 A2 | 4/2019 |

OTHER PUBLICATIONS

Pavliv, L, et al., "Formulation and Manufacturing", Drug and Biological Development : From Molecule to Product and Beyond, Ronald Evens, editor, Springer US, p. 210, 2007 (1 page).

Zhao, Xuebing, et al., "Preparation of Peracetic Acid from Acetic Acid and Hydrogen Peroxide : Experimentation and Modeling", The Chinese Journal of Process Engineering, vol. 8, No. 1, Feb. 2008 (7 pages).

"Peracetic Acid", from "Guideline for Disinfection and Sterilization in Healthcare Facilities", 2008 (last rev. 2016), CDC—Infection Control—Chemical Disinfectants, https://www.cdc.gov/infectioncontrol/guidelines/disinfection/disinfection-methods/chemical.html (2 pages).

Rutala, William, et al., "Guideline for Disinfection and Sterilization in Healthcare Facilities, 2008", Center for Disease Control, Dept. of Health and Human Services, USA, pp. 7-30 and 50-51, 2008 (158 pages).

"Acute Exposure Guideline Levels for Selected Airborne Chemicals", Committee on Acute Exposure Guideline Levels, Committee on Toxicology, & Board on Environmental Studies and Toxicology, National Research Council of the National Academies, The National Academies Press, Washington, D.C., vol. 8, Chapter 7, 2010, pp. 327-367 (44 pages).

Sattsangi, "A Microscale Approach to Chemical Kinetics in the General Chemistry Laboratory: The Potassium Iodide Hydrogen Peroxide Iodine-Clock Reaction", 2011, Journal of Chemical Education 88 (2), p. 184-188 (5 pages).

Sumner, "Peroxide and Vinegar Sterilization", Apr. 11, 2011, Cook's Info, http://web.archive.org/web/20160713134637/http://www.cooksinfo.com/peroxide-vinegar-sterilization (3 pages).

Hillsboro, Sanitizing with Vinegar and Hydrogen Peroxide, Mar. 29, 2012, The Urban Homestead, https://www.thriftyfun.com/tf23602306.tip.html (5 pages).

Nazzaro et al., "Effect of Essential Oils on Pathogenic Bacteria", 2013, Pharmaceuticals, vol. 6, p. 1451-1474 (24 pages).

Nyamunda, B. C., et al., Hydrogen Peroxide as an Oxidant for Organic Reactions, Journal of Atoms and Molecules, vol. 3, No. 1, Feb. 2013 (23 pages).

Hayashi et al., "Effect of Methylglyoxal on multidrug-resistant Pseudomonas aeruginosa", Apr. 2014, Frontiers in Microbiology, 5 (180):1-6 (6 pages).

"Common Chemicals Used for Cleaning and Decontamination Guideline", Department of Environmental Health and Safety, University of Colorado, Aug. 2014 (3 pages).

Shah et al., "Peracetic Acid Oxidation of Saline Waters in the Absence and Presence of H2O2: Secondary Oxidant and Disinfection Byproduct Formation", 2015, Environmental Science & Technology vol. 49, p. 1698-1705 (8 pages).

International Search Report and Written Opinion dated Jul. 24, 2017, for related International Application No. PCT/US2017/034519, filed May 25, 2017 (11 pages).

Extended European Search Report and Opinion dated May 2, 2019 in related European Application No. 18208959.9 filed Nov. 28, 2018 (7 pages).

International Search Report and Written Opinion dated May 7, 2019 for related International Application No. PCT/US2018/055367 filed Oct. 11, 2018 (20 pages).

(56) References Cited

OTHER PUBLICATIONS

First Office Action dated Sep. 14, 2020 in related Mexican Application No. MX/a/2018/014788 filed Nov. 29, 2018 (4 pages) with Google machine translation (3 pages).
First Office Action dated Jan. 19, 2021 in related Japanese Application No. 2019-514189 filed Nov. 22, 2018 (3 pages) with JPO machine translation (5 pages).
International Search Report and Written Opinion by the USPTO (as International Search Authority), dated Aug. 16, 2021, in related International Application No. PCT/US2021/021045 (12 pages).
First Office Action dated Jul. 14, 2021 in related Chinese Application No. 201811443773.1 filed Nov. 19, 2018 (6 pages) with Google machine translation (6 pages).
Second Office Action dated Jun. 22, 2021 in related Chinese Application No. 201780041206.0 filed Dec. 29, 2018 (8 pages) with Google machine translation (11 pages).
First Office Action dated Jul. 30, 2021 in related Chinese Application No. 201880079677.5 filed Jun. 10, 2020 (9 pages) with Google machine translation (8 pages).

* cited by examiner

METHOD FOR DISINFECTION OF ITEMS AND SPACES

Cross-reference to Related Application: This application is a Continuation Application of U.S. Ser. No. 16/202,269, filed on Nov. 28, 2018, which claims the benefit of the filing date of the Provisional Patent Application No. 62/591,812, filed on Nov. 29, 2017; is a Continuation-In-Part Application of U.S. Ser. No. 16/755,361, filed on Apr. 10, 2020, which is a National Stage Application of PCT/US2018/055367, filed on Oct. 11, 2018, which claims the benefit of the filing date of Provisional Patent Application No. 62/570,808, filed Oct. 11, 2017, the filing date of Provisional Patent Application No. 62/591,588, filed on Nov. 28, 2017, and the filing date of Provisional Patent Application No. 62/591,591, filed on Nov. 28, 2017; and is a Continuation-In-Part Application of U.S. Ser. No. 16/747,621, filed on Jan. 21, 2020, which is a Continuation Application of U.S. Ser. No. 16/198,570, filed on Nov. 21, 2018, issued as U.S. Pat. No. 10,603,396 on Mar. 31, 2020, which is a Continuation-In-Part Application of PCT/US2017/034519, filed on May 25, 2017, which claims the benefit of the filing date of Provisional Patent Application 62/341,799, filed on May 26, 2016, all of which are incorporated be reference for all purposes as if fully set forth herein.

FIELD OF THE INVENTION

The present invention is in the field of disinfection and sterilization methods.

BACKGROUND OF THE DISCLOSURE

There is a need for an inexpensive, effective, yet safe and convenient method to minimize the microbial burden of objects we interact with. This method must not leave behind microbes with resistance to future treatment. And, this need is becoming more compelling as microbes which are resistant to virtually all known antibiotics are becoming more common.

What is needed is a way to kill virtually all microbes in a way that they cannot develop a resistance to the antimicrobial. A potential way to do this would be to utilize ingredients and methods that are relatively safe to humans but are biocidal.

Iodine is a well-known, relatively safe biocide, more recently hydrogen peroxide has been shown to fight microbes and electricity has a biocidal effect. Sunlight, which emits energy in the ultraviolet wavelengths, is also well known for its biocidal properties.

The problem with these safe biocides is that each one individually is not effective against all types of microbes, and several target microbes have developed defense mechanisms against these biocides. However, combinations of two or more of these biocides have proven to work synergistically to enhance each one's effects. In particular, combining a salt of iodine with hydrogen peroxide has been shown to solve several problems with the use of iodine for disinfection. Thus, it is possible to include iodine into the array of safe biocides Iodine is an exceptional biocide because it is effective against virtually all types of microbes at relatively low dosage. In addition, it has several biocidal mechanisms so there is no known instance of microbes developing resistance to iodine after exposure.

Typically, iodine disinfectants have traditionally been used as leave-in-place, on-demand disinfectants. But they leave an unsightly color and other negative traits. Thus, if these negative traits of iodine are not wanted, it must be rinsed-away. When surfaces exceeding tens of square centimeters are to be treated by any of the common commercial forms of iodine, problems arise. There is either so much total iodine transferred to the surface resulting in large unsightly areas, or it requires a lot of post cleanup which is time consuming and expensive.

It is also time consuming and expensive to apply the traditional iodine antiseptics to surfaces exceeding tens of square centimeters. They are traditionally painted on which is time consuming and thus expensive. A cheaper method would be to spray it on. However, that leads to safety issues.

Inhalation of elemental iodine is problematic and more toxic to humans than hydrogen peroxide or iodine salts such as potassium iodide. For example, elemental iodine is considered a poison if dosed internally whereas an iodine salt such as potassium iodide is used as a medicine and a common food additive.

Another safety concern is the droplet size emitted by a sprayer. If it emits droplets smaller in size than about 10 microns it can lead to deep lung penetration which worsens any health concerns. On the other hand, if they are larger than 50 to 80 microns their "hang time" is not sufficient to arrive at distant surfaces because of gravity.

As a result, there is still a need for sterilization and disinfecting methods utilizing iodine that are simultaneously effective, convenient, and safe.

SUMMARY OF THE DISCLOSURE

The invention disclosed herein provides an improvement to disinfecting surfaces using iodine chemistry by eliminating instability, solubility and human safety issues associated with forming iodine at any point prior to application on a surface. The disclosed invention provides improved methods for disinfecting surfaces by dispersing iodine producing reactant compounds at very low levels in separate application steps and forming iodine biocides directly on surfaces to be disinfected.

The invention disclosed herein involves applying coatings of a low concentration of a safe iodine salt (such as potassium iodide) and, separately, a low concentration of hydrogen peroxide. Reactions between the iodine salt and hydrogen peroxide produce on surfaces to be treated produces low levels of elemental iodine ($I_2$) along with very low levels of HOI—which along with $I_2$ and $H_2O_2$ provide multiple mechanisms to kill microbes. The low levels of iodine biocide compounds produced by this method does not create the safety, color or odor problems associated with traditional iodine containing disinfectants.

Another aspect of safety is the droplet size emitted by a spray delivery device. The preferred method does not deliver droplets smaller in size than about 10 microns nor does it deliver droplets larger than 50 to 80 microns whose "hang-time" is not sufficient to arrive at distant surfaces because of gravity. "Hang-time" is the amount of time it takes a droplet of a certain diameter to fall one meter under the influence of gravity. Smaller diameter droplets have a considerably longer hang-time than larger diameter droplets.

Both of the above benefits (safety and "hang-time") are enhanced by electrostatics in that charged droplets repel each other (increasing "hang-time") and are attracted to surfaces including the nasal cavity, thus further reducing deep lung penetration.

Another advantage of this method is the ability of all the components to volatilize after the sterilization is complete.

The invention disclosed herein provides a way to have an effective iodine leave-in-place disinfectant that does not have residual color, odor or other undesirable effects. Combined with a surface layer that does not exceed 15 microns or preferably 6 microns, the small amount of material applied, and the volatility of the ingredients assures rapid evaporation. Thus, a room or item that has been treated can be quickly returned to service without the need for additional treatments to remove components from treated surfaces.

In one aspect, the disclosure provides a method of disinfecting a surface in need of disinfecting within an area, comprising the steps of: a) dispersing into the area a multiplicity of droplets of a first aqueous composition comprising a first iodine reactant compound that is either a peroxide compound or an iodine salt compound: b) allowing a time sufficient for the first aqueous composition to distribute throughout the area, and to deposit and coalesce into a layer upon the surface: c) dispersing into the area a multiplicity of droplets of a second aqueous composition comprising a second iodine reactant compound that is the other of the first iodine reactant compound, and: d) allowing a second time sufficient for the droplets of the second aqueous composition to deposit onto the coalesced layer of the first aqueous composition, thereby forming iodine and other iodine biocides in situ and disinfecting the surface.

In another aspect, the first aqueous composition is dispersed in an amount sufficient to provide the coalesced layer of the first aqueous composition with a substantially uniform thickness of at least about 1 micron and up to about 20 microns. In another aspect, the amount of the dispersed first aqueous composition is sufficient to provide the coalesced layer of the first aqueous composition with a substantially uniform thickness of at least about 3 microns and up to about 20 microns.

In another aspect, the second aqueous composition is dispersed in an amount sufficient to provide a coalesced layer of the second aqueous composition with a substantially uniform thickness of at least about 1 micron and up to about 20 microns.

In another aspect of the disclosure, at least one of the first aqueous composition or the second aqueous composition can also include other biocide compounds, including but not limited to alcohols and essential oils.

In another aspect of the disclosure, the method further includes the step of illuminating either or both of the first and second reactant compound and/or the surface on which they deposit within the area with a wavelength consisting essentially of ultraviolet light.

In another aspect of the disclosure, the multiplicity of droplets of the first aqueous composition is electrostatically charged.

In another aspect, the multiplicity of electrostatically charged droplets of the first aqueous composition are negatively charged or the multiplicity of electrostatically charged droplets of the first aqueous composition are positively charged.

In another aspect of the disclosure the charge polarity of the sprayer when it sprays the first and the second compound is optimized to provide the most desirable reaction of the first and second compounds.

In another aspect of the disclosure, the multiplicity of droplets of the second aqueous composition is electrostatically charged with the opposite polarity of the first aqueous composition.

In another aspect, the multiplicity of electrostatically charged droplets of the second aqueous composition are negatively charged or the multiplicity of electrostatically charged droplets of the second aqueous composition are positively charged.

In another aspect of the disclosure, the surface in need of disinfecting is grounded.

In another aspect, the disclosure provides a method of disinfecting a surface in need of disinfecting within an area, comprising the steps of: a) dispersing into the area a multiplicity of electrostatically-charged droplets of a first aqueous composition comprising a biocidal compound selected from the group consisting of: i) a peroxide compound or an iodine salt, ii) an alcohol, iii) an essential oil; b) allowing a first time sufficient for the first aqueous composition to distribute throughout the area, and to deposit and coalesce into a layer upon the surface; c) dispersing into the area a multiplicity of droplets of a second aqueous composition comprising a different one of the biocidal compound, and; d) allowing a second time sufficient for the droplets of the second aqueous composition to deposit onto the coalesced layer of the first aqueous composition, thereby disinfecting the surface.

In another aspect, the disclosure provides a method of disinfecting a surface, comprising the steps of: a) spraying electrostatically a first aqueous composition comprising a peroxide compound, toward and into contact with the surface; b) spraying a second aqueous composition comprising an iodine salt toward and into contact with the first aqueous composition on the surface, and; c) allowing the second aqueous liquid composition to contact the first aqueous liquid composition, thereby forming iodine biocides in situ and disinfecting the surface.

In another aspect, the disclosure provides a method of disinfecting a surface in need of disinfecting within an area containing ambient air, comprising the steps of: a) heating a first aqueous composition comprising a peroxide compound to produce a vapor comprising the peroxide compound in the ambient air; b) allowing a first time sufficient for the vapor comprising the peroxide compound to distribute throughout the area, and to cool, condense and deposit into a liquid layer upon the surface, the liquid layer comprising the peroxide compound; c) heating a second aqueous composition comprising an iodine salt compound, and; d) allowing a second time sufficient for the iodine salt compound to distribute throughout the area, and to cool and deposit the iodine salt compound onto the liquid layer comprising the peroxide compound, thereby forming an iodine biocide in situ and disinfecting the surface.

In another aspect of the disclosure, the first aqueous composition is heated at about 250° C.

In another aspect of the disclosure, the first aqueous composition and the second aqueous composition are cooled to about 55° C. to condense and deposit onto surfaces within the area to be disinfected.

In another aspect of the disclosure, the first aqueous composition and the second aqueous composition are comprised of food-grade components.

In another aspect, the disclosure provides a method of disinfecting a surface in need of disinfecting within an area containing ambient air, comprising the steps of: a) introducing a first aqueous composition comprising a peroxide compound into a first hot gaseous stream to produce a vapor comprising the peroxide compound, and discharging the first hot gaseous stream comprising the peroxide compound vapor into the ambient air; b) allowing a first time sufficient for the vapor comprising the peroxide compound to distribute throughout the ambient air of the area, and to cool, condense and deposit into a liquid layer upon the surface, the liquid layer comprising the peroxide compound; c) introducing a second aqueous composition comprising an iodine salt compound into a second hot gaseous stream and discharging the second hot gaseous stream comprising the iodine salt compound into the ambient air, and; d) allowing a second time sufficient for the iodine salt compound to distribute throughout the ambient air of the area, and to cool and deposit the iodine salt compound onto the first liquid layer comprising the peroxide compound, thereby forming an iodine biocide in situ and disinfecting the surface.

DETAILED DESCRIPTION OF THE INVENTION

The present disclosure relates to a method for sterilizing rooms, areas, and surfaces within those areas; particularly by generating iodine biocides on those targets in situ by applying iodine biocide reactant compounds in two or more separate applications. The method described herein is safer because the iodine biocides are formed directly on the target only after all reaction components have been applied.

The term, “health care surface” refers to a surface of a surface of an instrument, a device, a cart, a cage, furniture, a structure, a building, or the like that is employed as part of a health care activity.

As used herein, the term, “in situ,” refers to the production of an iodine biocide directly on the target surface, after application of two separate compositions containing iodine reactant compounds. This is distinct from other sterilization or disinfection methods that utilize the term in situ to describe the location at which two or more reaction mixtures are first mixed in a reaction vessel to form an iodine biocide, before subsequently applying the iodine biocide onto a surface or area.

As used herein, the term, “instrument,” refers to the various medical or dental instruments or devices that can benefit from cleaning with a composition according to the present disclosure.

As used herein, the term “microorganism” refers to any noncellular or unicellular (including colonial) organism. Microorganisms include all prokaryotes. Microorganisms include bacteria (including cyanobacteria), spores, lichens, fungi, protozoa, virinos, viroids, viruses, phages, and some algae. As used herein, the term “microbe” is synonymous with microorganism.

As used herein, the phrase, “iodine salt”, refers to any salt of iodine that is capable of forming an iodine biocide that is effective as a disinfecting agent.

As used herein, the term, “iodine biocide compound” refers to any compound that can react with an iodine salt to form an iodine biocide, including but not limited to hydrogen peroxide, metal peroxides, and ozone.

As used herein, the term “polyhydric alcohol” refers to an alcohol that has two or more hydroxyl groups. Polyhydric alcohols suitable for use in the aqueous compositions include but are not limited to sugars, sugar alcohols, and non-aliphatic polyhydric alcohols such as phenols.

Concentrations, dimensions, amounts, and other numerical data may be presented herein in a range format. It is to be understood that such range format is used merely for convenience and brevity.

In accordance with these definitions, several methods for disinfecting target surfaces within an area by forming iodine biocides on those surfaces in situ are provided. The potential applications for these methods are extraordinarily diverse, including but not limited to disinfecting animal living spaces, food products and processing surfaces, health care surfaces and instruments, laboratories, restrooms, vehicles, schools, offices, public transportation, industrial facilities, and countless other areas and surfaces. This disclosure overcomes the deficiencies associated with direct delivery of iodine for sterilization, particularly with regard to the instability, insolubility and safety of iodine biocides.

This disclosure harnesses the power of iodine chemistry to disinfect target surfaces while utilizing ingredients that are safe and have a very long shelf life and that anyone can obtain at their local grocery store or pharmacy.

Without being limited by theory, the antimicrobial action of iodine is quick and effective at low concentrations, and thus it is used in operating theatres. It is believed to penetrate into microorganisms and attack particular amino acids (such as cysteine and methionine), nucleotides, and fatty acids, ultimately resulting in cell death. It also has an antiviral action. It may also destabilize membrane fatty acids by reacting with unsaturated carbon bonds.

It is believed that peroxides are effective as disinfectants because they are powerful oxidizing agents that can irreversibly damage proteins and DNA within microorganisms. Additionally, peroxides can reactivate iodine if it is reduced to iodide by oxidizing it. Thus, lower levels of iodine are required because peroxides can recycle iodide back to the iodine active state.

Alcohols are also believed to be effective biocides denaturing cell walls of microbes making it harder for them to control their cell contents. This mechanism would also reduce a microbe’s ability to resist the penetration of iodine and peroxides. It also helps other biocides work by lowering the surface tension of water.

Used together, the various components of this disclosure work together to produce an exceptional microbe kill by a large number of differing mechanisms. This makes it virtually impossible for a microbe to acquire immunity.

Essentially, this disclosure provides a method for disinfecting surfaces within an area that needs disinfecting, the method comprising the steps of: dispersing into the area a multiplicity of droplets of a first aqueous composition comprising a first iodine biocide reactant compound; allowing a time sufficient for the first aqueous composition to distribute throughout the area, and to deposit and coalesce into a layer about the surfaces; dispersing a multiplicity of droplets of a second aqueous composition comprising a second iodine biocide reactant compound; and allowing a second time sufficient for the second aqueous composition to deposit onto the coalesced layer of the first aqueous composition, thereby forming an iodine biocide in situ and disinfecting the surfaces.

So long as an iodine biocide is formed only on the surface to be disinfected, the effectiveness of the method is independent of the order in which the iodine biocide reactant compounds are dispersed. Thus, the first iodine biocide reactant compound can either be an iodine salt compound or a peroxide compound, so long as the second iodine biocide reactant compound is the opposite compound of that chosen to be the first iodine biocide reactant compound.

The peroxide compound present in either aqueous composition is any compound that can react with an iodine salt to form an iodine biocide. Generally, these will include but not be limited to hydrogen peroxide, metal peroxides, or ozone. In some embodiments, the peroxide compound is hydrogen peroxide. The peroxide compound may be present in an aqueous composition at concentrations ranging from about 0.1% to about 10% by weight.

The iodine salt compound present in either aqueous composition is any iodine salt that can effectively form an iodine biocide by reacting with a peroxide compound. Non-limiting examples of compounds which can be used include hydrogen iodide, sodium iodide, and potassium iodide. The iodine salt may be present in an aqueous composition at concentrations ranging from about 0.01% to about 10% by weight.

In some embodiments of the disclosure, the disinfectant methods described above for generating iodine biocides on surfaces to be disinfected can be used for a variety of user-identified biocidal and/or anti-microbial purposes, including antimicrobial, bleaching, or sanitizing applications.

In some embodiments, the iodine biocides generated according to the method of the present disclosure are effective for killing one or more of the pathogenic bacteria associated with a health care surfaces and instruments including but not limited to, *Salmonella typhimurium, Staphylococcus aureus, Salmonella choleraesurus, Pseudomonas aeruginosa, Escherichia coli*, Mycobacteria, yeast, and mold. In other embodiments, the generated iodine biocides are also effective in domestic or industrial applications and can be applied in a variety of areas including but not limited to kitchens, bathrooms, factories, hospitals, dental offices, restaurants, laundry or textile services, animal stalls and food processing plants.

Furthermore, the iodine biocides generated according to the method of the present disclosure are effective against a wide variety of microorganisms, such as Gram-positive organisms (*Listeria monocytogenes* or *Staphylococcus aureus*), Gram-negative organisms (*Escherichia coli* or *Pseudomonas aeruginosa*), catalase-positive organisms (*Micrococcus luteus* or *Staphylococcus epidermidis*), or sporulent organisms (*Bacillus subtilis*).

The disclosure is illustrated by the following examples:

EXAMPLES

The following example illustrates the embodiments of the disclosure that are presently best known. However, it is to be understood that the following is only illustrative of the application of the principles of the present disclosure. Numerous modifications and alternative compositions, methods, and systems may be devised by those skilled in the art without departing from the spirit and scope of the present disclosure.

Example 1: Closed-System Electrospray Distribution and Log-Kill Studies

A study was conducted in accordance with embodiments of the present disclosure to determine the antimicrobial effect of a method where an iodine biocide is formed on target surfaces within a 1 cubic meter translucent plastic cube in situ by applying two separate aqueous compositions, one containing potassium iodide and one containing hydrogen peroxide. The following ingredients are included in approximate amounts:
First Aqueous Composition:
0.64% (w/w) potassium iodide
15% (w/w) Ethanol
0.003% (w/w) Cinnamon Oil
84.357% (w/w) Distilled Water
Second Aqueous Composition:
5.25% (w/w) Hydrogen Peroxide
15% (w/w) Ethanol
79.75% (w/w) Distilled Water To simultaneously evaluate whether an electrospray device would evenly distribute an aqueous composition including an iodine biocide reactant compound, the first aqueous composition is applied using a Hurricane ES™ Portable Electrostatic Aerosol Applicator. Two analytical balances are placed inside the cube and connected to a computer station configured to collect and record mass measurements as a function of time. On each balance, a 1000 square centimeter plastic sheet is placed on the balance weighing pan. The position of each balance is staggered to be in different positions along the x, y, and z axes in relation to the position of the electrostatic sprayer. The second aqueous composition is applied using a hand sprayer.

Cultures from commercially-available strains of three species of bacteria—*Bacillus subtilis, Micrococcus luteus*, and *Staphylococcus epidermis*—are selected for the log-kill studies because they possess several known defense mechanisms to common biocides while at the same time having different physical properties from each other. Sterilized, pre-poured agar plates are used as growth media to produce colonies of each bacteria. Eight plates are inoculated for each species. Of those 8 plates, 4 plates are exposed to the aqueous compositions that contain the iodine biocide reactant compounds, and 4 are held out as controls. Plates are inoculated using the standard T-method of streaking for log-kill studies, where the concentration of bacteria in the fourth quadrant of the plate is approximately 1,000,000× diluted with respect to the first quadrant. The test plates for each species are then placed inside the cube. After the cube is closed, the lids are opened. Control plates are sealed with tape.

The first aqueous composition is then applied to the entire cube by electrospray for 30 seconds with a set particle size of about 15 to 60 microns. During the application, mass measurements from the two balances are collected and recorded by the computer. The time of application is selected to provide a 3 microns thick coating within the treatment space as measured by the balances. After about 1 minutes, the second aqueous composition is applied using a hand sprayer, and the entire system is untouched for another 5 minutes. Lids are replaced on each of the test plates inside the cube before being brought out into the ambient environment, where they are sealed with tape. The sealed test plates and the control plates are then incubated at about 28° C. and inspected after 1, 2, and 4 days.

The results of the tests are provided as follows:

TABLE 1

| Electrospray Distribution Mass - First Aqueous Composition (g) | |
|---|---|
| Balance A (with 1000 cm^2 plate) | 0.201 |
| Balance B (with 1000 cm^2 plate) | 0.195 |

TABLE 2

| Presence of colonies after 1 day (+ or −) | | | |
|---|---|---|---|
| Plate Number | B. subtilis | M. luteus | S. epidermis |
| 1 | − | − | − |
| 2 | − | − | − |
| 3 | − | − | − |
| 4 | − | − | − |

TABLE 3

| | Presence of colonies after 2 days (+ or –) | | |
|---|---|---|---|
| Plate Number | B. subtilis | M. luteus | S. epidermis |
| 1 | – | – | – |
| 2 | – | – | – |
| 3 | – | – | – |
| 4 | – | – | – |

TABLE 4

| | Presence of colonies after 4 days (+ or –) | | |
|---|---|---|---|
| Plate Number | B. subtilis | M. luteus | S. epidermis |
| 1 | – | – | – |
| 2 | – | – | – |
| 3 | – | – | – |
| 4 | – | – | – |

The mass of the first aqueous composition deposited on balance A and balance B indicates a difference of 0.006 grams which is only a 3% difference. In combination with a qualitative observation that the inside surfaces of the cube appear to be equally coated with liquid, it is believed that the electrospray evenly distributes the first aqueous composition within the cube.

All controls produce the expected results, with positive control plates not treated with aqueous compositions containing iodine biocide reactant compounds showing characteristic growth for each organism. Over the 16 control plates, there is an average of 4 or 5 colonies in the fourth quadrant of the plate, indicating that there are 45,000,000 colonies in the initial inoculation.

Therefore, the lack of colonies on the test plates, coupled with the approximately 45,000,000 colonies observed on the control plates, indicates that the method is effective to at least a log-6 kill rate, representing a kill of 99.9999% of the bacteria originally present on the plate.

Example II: Fifteen Petri dishes containing nutrient agar were streaked with *Bacillus subtilus* in three zones in the traditional manner. Five of the Petris were sealed after streaking (control). Five Petris were sprayed with a solution containing 2 ppm KI and 10% ethanol, sufficiently to wet the surface, and then sealed. And, five Petris were initially sprayed as before, and then subsequently sprayed with a solution containing 5% hydrogen peroxide and 2.5% isopropanol, and then sealed.

After incubating all 15 Petri dishes at 40° C. for three days, the number of colony forming units was estimated as follows: about 10k for the control; about 6k for the KI control and "0" for the double spray test.

While particular embodiments of the disclosure have been described, the disclosure can be further modified within the spirit and scope of this disclosure. Those skilled in the art will recognize, or be able to ascertain using no more than routine experimentation, numerous equivalents to the specific procedures, embodiments, claims, and examples described herein.

It is also understood by those familiar with the art that from the Summary of the Disclosure to the Example, the word "bromine" can be substituted for the word "iodine" and the word "bromide" can be substituted for the word "iodide" because as a neighboring halide, its reactions with peroxide are similar to iodine and its ability to kill microbes is also similar to iodine. Furthermore, it will also be apparent and understood by the practitioners of the art that the salts of bromine and iodine are compatible and can be used together and concurrently in biocidal formulations.

The invention claimed is:

1. A method of disinfecting a surface in need of disinfecting, within an area, using an iodine reactant system having two reactant compounds that consist of a peroxide compound and an iodine salt compound, said method comprising the steps of:

dispersing into said area a multiplicity of droplets of a first aqueous composition comprising water and a first reactant compound of the iodine reactant system that is the peroxide compound or the iodine salt compound;

allowing a time sufficient for said droplets of the first aqueous composition to distribute throughout the area and to deposit and coalesce into a layer upon said surface;

dispersing into said area a multiplicity of droplets of a second aqueous composition comprising water and a second reactant compound of the iodine reactant system that is the peroxide compound or the iodine salt compound that is different than the first reactant compound; and, allowing a second sufficient time for the droplets of the second aqueous composition to deposit onto the coalesced layer of the first aqueous composition to form a reaction layer; thereby forming the iodine reactant system and producing a biocide reactant compound consisting of iodine in situ in the reaction layer, and disinfecting said surface.

2. A method of disinfecting a surface in need of disinfecting, within an area, using an iodine reactant system having two disinfecting reactant compounds that consist of a peroxide compound and an iodine salt compound, said method comprising the steps of:

dispersing into the area a multiplicity of droplets of a first aqueous composition comprising water and a first disinfecting reactant compound of the iodine reactant system that is the peroxide compound or the iodine salt compound;

allowing a time sufficient for said droplets of the first aqueous composition to distribute throughout the area and to deposit and coalesce into a layer upon said surface;

dispersing into the area a multiplicity of droplets of a second aqueous composition comprising water and a second disinfecting reactant compound of the iodine reactant system that is the peroxide compound or the iodine salt compound that is different than the first disinfecting reactant compound; and allowing a second sufficient time for the droplets of the second aqueous composition to deposit onto the coalesced layer of the first aqueous composition to form a reaction layer comprising the iodine reactant system, thereby forming a biocide reactant compound consisting of iodine in situ in the reaction layer, and disinfecting said surface, wherein the iodine salt compound is present in the first aqueous composition or the second aqueous composition at a concentration of from about 0.01% to about 10% by weight, and wherein the peroxide compound is present in the other of the first aqueous composition or the second aqueous composition at a concentration of from about 3% to about 7% by weight.

3. The method of claim 2 wherein an amount of the dispersed first aqueous composition is sufficient to provide the coalesced layer of the first aqueous composition with a substantially uniform thickness of at least 1 micron and up to about 20 microns.

4. The method of claim 3 wherein the amount of the dispersed second aqueous composition is sufficient to provide a coalesced layer of the second aqueous composition with a substantially uniform thickness of at least 1 micron and up to about 20 microns.

5. The method of claim 4 wherein the amount of the dispersed first aqueous composition is sufficient to provide the coalesced layer of the first aqueous composition with a substantially uniform thickness of at least 3 microns and up to about 20 microns.

6. The method of claim 2 wherein the multiplicity of droplets of the first aqueous composition are electrostatically charged droplets.

7. The method of claim 6 wherein the multiplicity of electrostatically charged droplets of the first aqueous composition are negatively charged.

8. The method of claim 6 wherein the multiplicity of electrostatically charged droplets of the first aqueous composition are positively charged.

9. The method of claim 2 wherein the multiplicity of droplets of the second aqueous composition are electrostatically charged droplets.

10. The method of claim 9 wherein the multiplicity of electrostatically charged droplets of the second aqueous composition are negatively charged.

11. The method of claim 9 wherein the multiplicity of electrostatically charged droplets of the second aqueous composition are positively charged.

12. The method of claim 2 wherein the first aqueous composition comprises potassium iodide.

13. The method of claim 2, wherein the first disinfecting reactant compound is the iodine salt compound and the second disinfecting reactant compound is the peroxide compound.

14. The method of claim 13 wherein the second aqueous composition comprises hydrogen peroxide.

15. The method of claim 2, wherein at least one of the first aqueous composition and the second aqueous composition comprises an alcohol.

16. The method of claim 15, wherein the first aqueous composition and the second aqueous composition each comprises the alcohol.

17. The method of claim 16, wherein the alcohol comprises ethanol.

18. The method of claim 16, wherein the alcohol of the second aqueous composition comprises isopropanol.

19. The method of claim 2 wherein the droplets of the first aqueous composition and the droplets of the second aqueous composition are from about 10 microns to about 80 microns in size.

20. The method of claim 19 wherein the droplets of the first aqueous composition are from about 15 microns to about 60 microns in size.

* * * * *